(12) United States Patent
Blanchard et al.

(10) Patent No.: US 6,274,163 B1
(45) Date of Patent: *Aug. 14, 2001

(54) KERATINOUS PROTEIN MATERIAL FOR WOUND HEALING APPLICATIONS AND METHOD

(75) Inventors: Cheryl R. Blanchard, San Antonio, TX (US); Robert A. Smith, Jackson, MI (US); Arlene J. Siller-Jackson, Holotes, TX (US)

(73) Assignee: Keraplast Technologies, Ltd., San Antonio, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/057,161

(22) Filed: Apr. 8, 1998

(51) Int. Cl.[7] ............... A61F 13/00; A61K 9/70; A61L 15/00
(52) U.S. Cl. ............... 424/443; 424/445
(58) Field of Search ............... 128/156; 424/443, 424/70.1, 61, 445

(56) References Cited

U.S. PATENT DOCUMENTS

| | | | |
|---|---|---|---|
| 2,993,794 | 7/1961 | Moshy | 99/18 |
| 4,135,942 | * 1/1979 | Kikkawa | 106/155 |
| 4,141,888 | 2/1979 | Matsuda et al. | 260/123.7 |
| 4,570,629 | * 2/1986 | Widra | 128/156 |
| 4,711,780 | * 12/1987 | Fahim | 424/145 |
| 4,818,520 | * 4/1989 | Fleischner | 424/61 |
| 4,983,580 | 1/1991 | Gibson | 514/2 |
| 5,047,249 | * 9/1991 | Rothman | 424/543 |
| 5,258,043 | 11/1993 | Stone | 623/66 |
| 5,276,138 | * 1/1994 | Yamada | 530/357 |
| 5,358,935 | 10/1994 | Smith et al. | 514/21 |
| 5,487,889 | 1/1996 | Eckert et al. | 424/93.1 |
| 5,639,448 | 6/1997 | Galleguillos et al. | 424/70.11 |
| 5,712,252 | 1/1998 | Smith | 514/21 |
| 5,763,583 | * 6/1998 | Arai | 530/353 |
| 5,866,167 | * 2/1999 | Van Bossuyt | 424/520 |

FOREIGN PATENT DOCUMENTS

| | | |
|---|---|---|
| 531446 | 1/1941 | (DE) . |
| 6-100600 | 4/1994 | (JP) . |

OTHER PUBLICATIONS

Yu et al., "Human Hair Keratins", *The Journal of Investigative Dermatology*, vol. 101, No. 1, 1993, 4 pages.

Stedman's Medical Dictionary, 26th Edition, Williams & Wilkins, published on date even with or prior to Apr. 8, 1998, 2 pages.

Cohly, et al., "Effect of Processed hair on Wound Healing Parameters," Wound Repair and Regeneration 5, Part 1, A108, Apr. 7, 1997.

Cohly, et al., "Role of Proceed Hair on Hydrogen Peroxide–Induced Human Dermal Fibroblast Cell Injury," Repair and Regeneration, 5, Part 3, A270, Nov. 11, 1997.

(List continued on next page.)

*Primary Examiner*—Thurman K. Page
*Assistant Examiner*—S. Howard
(74) *Attorney, Agent, or Firm*—Timothy S. Corder; Stephen J. Moloney; Vinson & Elkins L.L.P.

(57) ABSTRACT

A keratinous wound healing material, preferably derived from the hair of the patient or a compatible donor. Keratin powder can be derived from hair using processing steps including cleaning, suspending in a liquid carrier, homogenizing and removing the liquid. The keratinous material may be applied to the wound in powder form. The keratin can also be applied in sheet form. The keratinous material can be bound with polymeric binder and formed into a sheet by pouring the polymer/binder solution into a mold and flashing off the solvent.

67 Claims, 5 Drawing Sheets

Effect of KP on Human Epidermal Keratinocytes

OTHER PUBLICATIONS

Cohly, et al., Effect of Processed Hair on Partial Thickness Wounds in Rats and Regeneration, 5, Part 3, A270, Nov. 11, 1997.

Cohly, et al., "Effect of Proceed Hair (PH) on Partial Thickness Wound in Rats," Journal of the Mississippi Academy of Sciences, 43:50, Jan. 1998.

Cohly, et al., "Role of Processed Hair on Hydrogen Peroxide–Induced Human Dermal Fibroblast (F) Cell Injury," Journal of the Mississippi Academy of Sciences, 43:50, Jan. 1998.

Cohly, et al., "Effect of Processed Hair Scaffolding on Wound Healing Parameters," Mississippi Academy of Sciences, 43:51, Jan. 1998.

* cited by examiner

KERATINOUS PROTEIN MATERIAL FOR WOUND HEALING APPLICATIONS AND METHOD

FIELD OF THE INVENTION

The present invention is related to wound dressing materials. More specifically, the present invention is related to a keratin-based material applied directly to wounds to aid in the wound healing process.

BACKGROUND OF THE INVENTION

Chronic wounds can be caused by a variety of events, including surgery, prolonged bedrest and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers) and venous stasis disease, which can cause full thickness ulcers of the lower extremities. Full thickness wounds tend to heal very slowly. Proper wound care technique including the use of wound dressings is extremely important to successful chronic wound management. Chronic wounds affect an estimated four million people a year, resulting in health care costs in the billions of dollars. "Treatment of Skin Ulcers with Cultivated Epidermal Allografts," T. Phillips, O. Kehinde, and H. Green, *J. Am. Acad. Dermatol.*, V. 21, pp. 191–199 (1989).

The wound healing process involves a complex series of biological interactions at the cellular level which can be grouped into three phases: homeostasis and inflammation; granulation tissue formation and reepithelization; and remodeling. "Cutaneous Tissue Repair: Basic Biological Considerations," R. A. F. Clark, *J. Am. Acad. Dermatol.*, Vol. 13, pp. 701–725 (1985). Keratinocytes (epidermal cells that manufacture and contain keratin) migrate from wound edges to cover the wound. Growth factors such as transforming growth factor-$\beta$ (TGF-$\beta$) play a critical role in stimulating the migration process. The migration occurs optimally under the cover of a moist layer. Keratins have also been found to be necessary for reepithelization. Specifically, keratin types K5 and K14 have been found in the lower, generating, epidermal cells, and types K1 and K10 have been found in the upper, differentiated cells. Wound Healing: Biochemical and Clinical Aspects, I. K. Cohen, R. F. Diegleman, and W. J. Lindblad, eds., W. W. Saunders Company, 1992. Keratin types K6 and K10 are believed to be present in healing wounds, but not in normal skin. Keratins are major structural proteins of all epithelial cell types and appear to play a major role in wound healing.

An optimum wound dressing would protect the injured tissue, maintain a moist environment, be water permeable, maintain microbial control, deliver healing agents to the wound site, be easy to apply, not require frequent changes and be non-toxic and non-antigenic. Although not ideal for chronic wounds, several wound dressings are currently on the market, including occlusive dressings, non-adherent dressings, absorbent dressings, and dressings in the form of sheets, foams, powders and gels. Wound Management and Dressing, S.Thomas, The Pharmaceutical Press, London, 1990.

Attempts have been made to provide improved dressings that would assist in the wound healing process using biological materials such as growth factors. To date, these biologicals have proven very costly and, due to the lack of an appropriate delivery vehicle, have shown minimal clinical relevance in accelerating the chronic wound healing process. In cases of severe fall thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water permeable layer, but is rejected by the patient, usually within two weeks, and does not become part of the new epidermis.

What would be desirable, and has not heretofore been provided, is a wound dressing that protects the injured tissue, maintains a moist environment, is water permeable, maintains microbial control, is easy to apply, does not require frequent changes and is non-toxic and non-antigenic, and most important, delivers effective healing agents to the wound site.

SUMMARY OF THE INVENTION

The present invention includes a wound healing dressing containing the protein keratin. Keratin can be obtained from a number of sources including human or animal hair, and finger or toe nails, with the preferred source being hair from the patient or a compatible donor. A further preferred source is, in general, human hair. This avoids any deleterious effects related to allergies to animal tissue. Non-soluble keratin, as a wound healing agent, can be applied as a wound dressing to a wound in the form of a sheet or a powder. The term "non-soluble keratin" is used herein to describe a form of keratin that is nominally insoluble in a neutral aqueous environment. Experimentally, a low molecular weight fraction of keratin ranging from 45–200 kilodaltons does go into solution from aqueous suspensions containing the non-soluble keratin. Non-soluble keratin powder is obtained from hair using mechanical techniques. Hair can be processed mechanically by cleaning the hair with shampoo, suspending the hair in a liquid carrier, homogenizing the hair into keratin particles, removing the liquid carrier from the keratin, and sterilizing the resulting powder. See U.S. Pat. No. 5,358,935. A soluble form of keratin powder (the term "soluble keratin" as used herein describes a form of keratin that is nominally soluble in an aqueous environment) can be processed chemically by incubating the hair in a hair matrix dissolving solvent, separating the soluble and insoluble keratins, removing the solvent from the soluble keratins thereby creating a soluble keratin powder, and sterilizing the keratin powder. See U.S. patent application Ser. No. 08/979, 456, entitled "Keratin-Based Hydrogel for Biomedical Applications and Method of Production". This soluble keratin can then be used as a binder in a sheet wound dressing.

The non-soluble keratin powder can be further processed into a sheet wound dressing. To create a sheet dressing, a polymeric binder material is dissolved in a solvent such as acetone or ethanol. Non-soluble keratin powder can then be added to the solvent/polymer solution. The polymer/keratin suspension can be poured into molds, and the solvent flashed off, forming a sheet. The polymer/keratin suspension can also be cast into a sheet and the solvent flashed off. In addition, the sheet can be pressed with an applied nominal load of 200 lb., but could range from 10 lb. to 300 lb., for a time period ranging from 3 minutes to 3 hours at a temperature of 200° F., but could range from 100° F. to 300° F., to provide a coherent, flat sheet. The resulting sheet can be cut and shaped as needed before being applied to the wound. In addition, the soluble form of keratin can be used as the binder material, resulting in a wound healing sheet that is nominally all keratin, with the soluble component of the keratin able to easily resorb into the wound site.

Keratin can be applied directly to the wound in powder or sheet form. The keratin can also be incorporated into carriers including lotions, creams and gels. Applicants believe the applied keratin is supplying keratin to the wound site thereby accelerating the wound healing process. Keratin powder or sheets are easy to apply directly to a wound and provide a non-toxic, non-antigenic wound dressing that maintains wound moisture and protects the wound area, yet does not have to be replaced. Where keratin is obtained from the hair of the patient or a compatible donor, the keratin is particularly non-antigenic.

DETAILED DESCRIPTION OF THE PREFERRED EMBODIMENTS

One mechanical method for manufacturing a keratin powder includes technology described in U.S. Pat. No. 5,358,935, herein incorporated by reference. Hair is harvested from a human or animal source. The patient or a compatible donor is a preferred source of hair, as hair from these sources is most likely to result in a non-antigenic wound healing product. The hair is preferably washed in a mild detergent such as shampoo, and rinsed and drained thoroughly. The washed hair should be rinsed using a cheese cloth or other water permeable fabric. The hair is then preferably bleached in a mild, 3–15% solution of $H_2O_2$ for 15 minutes to 5 hours within a temperature range of 25° C. to 95° C. The bleaching step is not necessary and can be omitted, where a final product containing color pigments is acceptable. The hair is then chopped into shorter lengths.

The cleaned, chopped hair is placed in a liquid carrier such as water, ethanol, acetone or liquid nitrogen, and further reduced to a powder by homogenizing the hair with a rotor-stator assembly, such as the Omni 5000 Homogenizer (Omni International). A preferred carrier is liquid nitrogen, as it embrittles the hair, reducing the total processing time. The resulting suspension of protein particles includes particles having a major, larger dimension of about 0.1 μm to about 500 μm. The liquid carrier can then be evaporated, leaving a free-flowing keratin powder. The resulting powder can then be sterilized, using a steam autoclave or ethylene oxide.

By varying processing conditions and/or centrifuging to separate, the resulting keratin powder particles can be prepared to result in two size distributions. A fine powder ranges in major dimension from about 0.1 μm to about 100 μm, and has an aspect ratio ranging from about 1–4. Coarse, high aspect ratio whisker-shaped particles have a major dimension of about 100 μm to about 500 μm and an aspect ratio ranging from about 10–50.

A sheet wound dressing can be manufactured from the keratin powder described above. Polymer binder materials are used in the manufacture of the sheet dressings and can include non-resorbable polymers, bioresorbable polymers or the resorbable form of keratin. Resorbable polymers and the resorbable keratin are biologically resorbed over time through hydrolysis while the non-resorbable polymer binders are eventually physically removed from the wound site along with the non-resorbable keratin wound sheet. Suitable non-resorbable polymers include ethyl cellulose, cellulose acetate and polyethylene. Suitable bioresorbable polymers include polylactic acid, polyglycolic acid, and their copolymers. The amount of binder used can range from about 3 weight percent to about 50 weight percent, relative to the protein powder. To process the sheets, the polymer or keratin binder, preferably in a granulated or powder form, is added to an appropriate solvent such as acetone or ethanol and dissolved. The non-resorbable keratin powder can then be added to the solvent/polymer solution and mixed thoroughly to ensure homogeneity in the final sheet product.

The combination of fine to coarse powder can be varied to create different products. Using 100% fine powder will result in a smooth, thin, flexible product. Adding the coarse material will increase the mechanical integrity of the final product, but will result in a stiffer wound healing sheet material. A preferred composition utilizes a 50%/50% mixture of fine and coarse powder, and 3 weight % polymer binder. The non-resorbable protein powders can be added to the solvent in a concentration ranging from about 50 weight % to about 97 weight %.

The polymer/protein suspension can then be formed into sheets of the desired size. One method of sheet formation includes pouring the suspension into molds and flashing off the solvent either by heating the molds or placing them in a warm environment such as an oven, or by placing them in a vacuum. Another method includes molding, flashing off the solvent, then pressing the material at an elevated temperature to further consolidate the sheet. Yet another method includes casting the material into a sheet and flashing of the solvent. The final sheet can then be sterilized using radiation, a steam autoclave or ethylene oxide. The keratin wound healing sheets can be cut and shaped as needed using scissors before being applied to the wound.

Anti-bacterial additives, ointments and biologicals such as growth factors or collagen can be added to both the powder and sheet forms of the keratin wound dressing. Bactericidal ointment or a suspension of antibiotics or biologicals can be impregnated into the sheet dressing by passing a blade having the additive at its front over the sheet, thereby evenly distributing the additive over the sheet. Alternatively, the sheet material can be soaked in a solution containing the desired additive and the additive allowed to precipitate onto the surface of the sheet. The solvent can then be flashed off, leaving the sheet material impregnated and coated with the desired additive.

Figure 1:
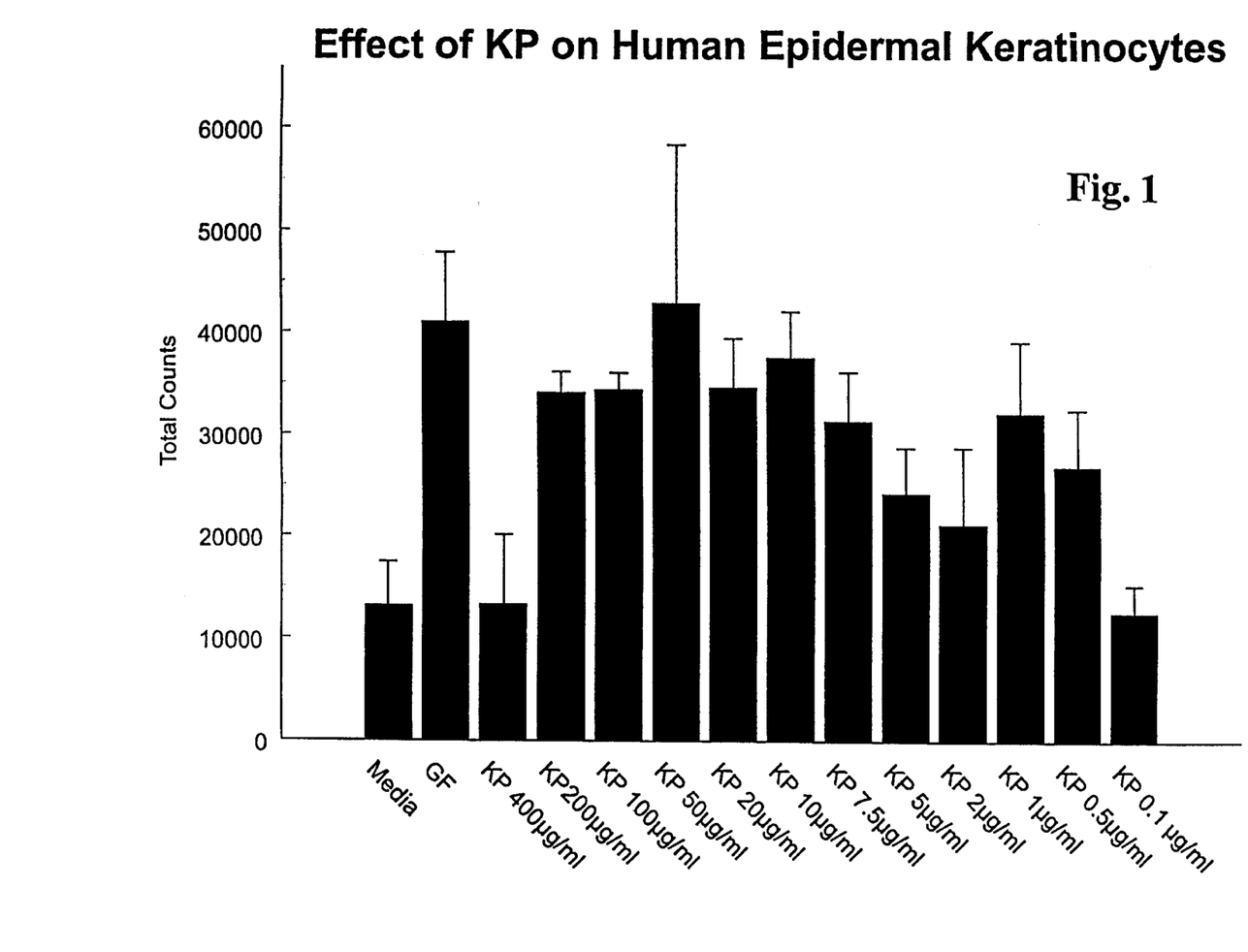
FIG. 1 is a graph showing the effect of varying concentrations of KP (keratin powder) on human epidermal keratinocytes relative to cell media alone (media) and a known growth factor (GF)
Figure 2:
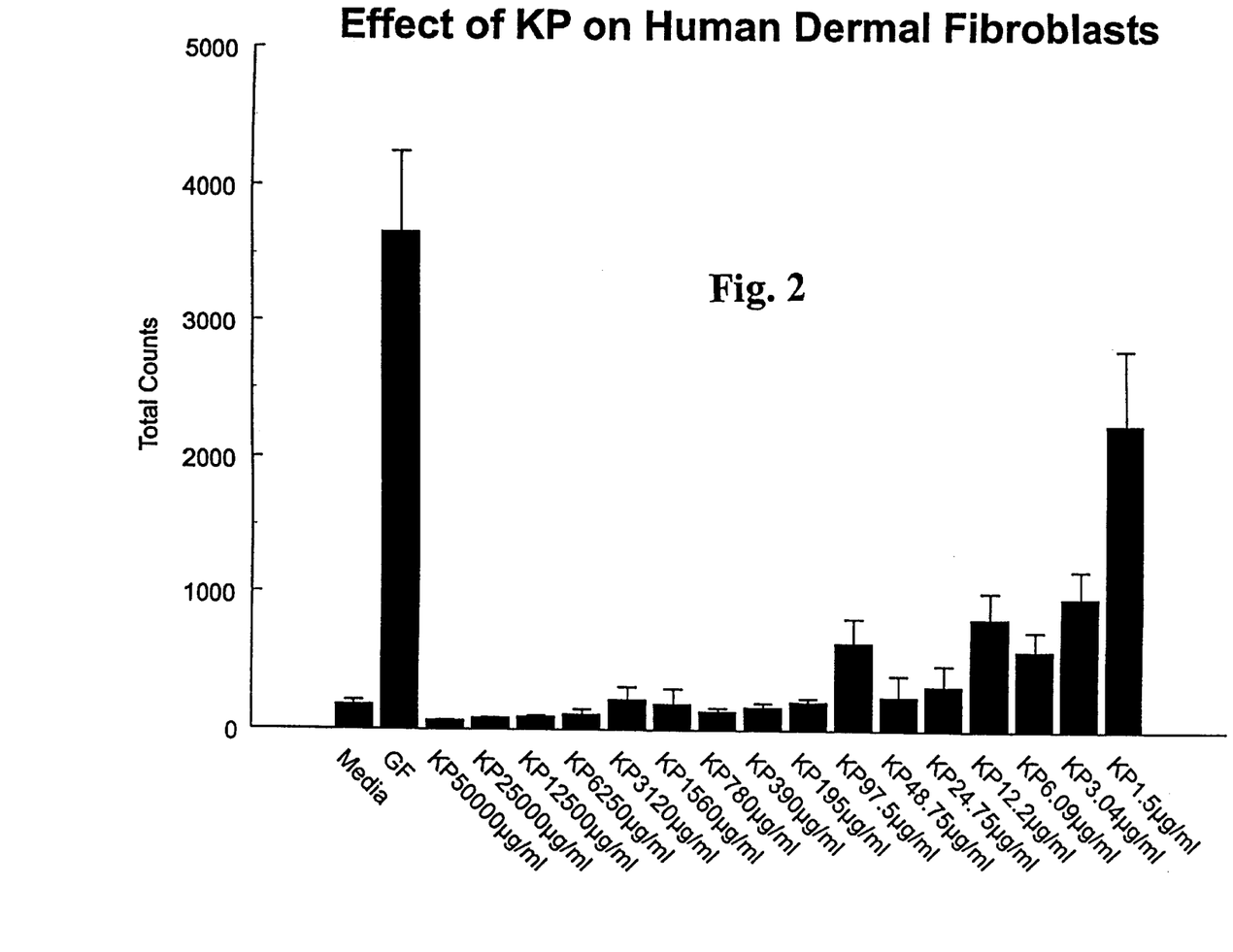
FIG. 2 is a graph showing the effect of varying concentrations of KP on human dermal fibroblasts relative to cell media alone (media) and a known growth factor (GF)
Figure 3:
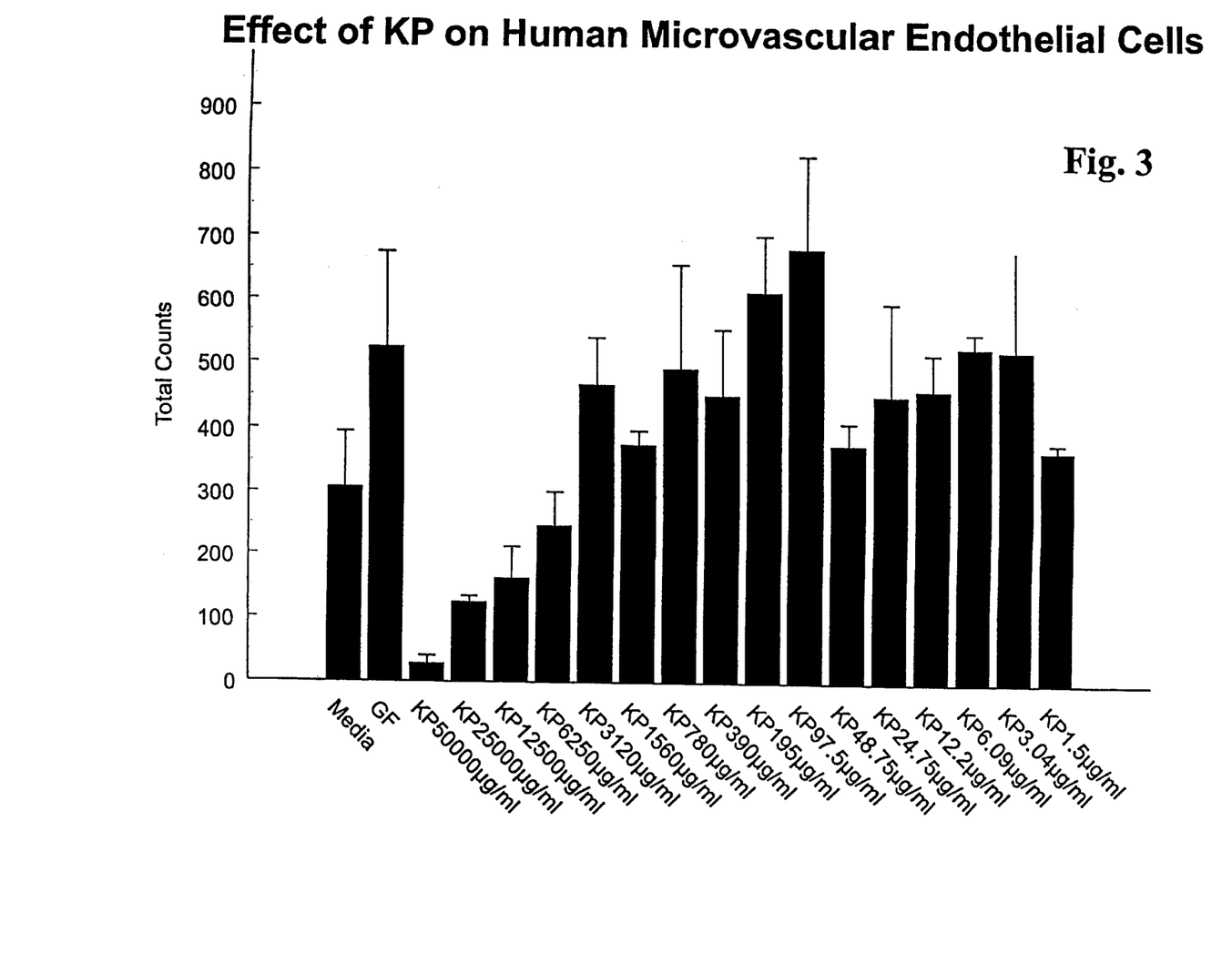
FIG. 3 is a graph showing the effects of varying concentrations of KP on human microvascular endothelial cells relative to cell media alone (media) and a known growth factor (GF)

The use of non-resorbable keratin materials in promoting wound healing was demonstrated in several experiments. In a first experiment, keratin powder derived from human hair was incubated with cell culture media. The media/hair mixture was passed though a micro filter. Wound healing cell lines, including microvascular endothelial cells, keratinocytes and fibroblasts, were placed in culture using this media extract. Cell proliferation was measured through tritiated thymidine uptake. Significant proliferation of these wound healing cells was measured. Specifically, keratinocytes proliferated profusely, fibroblasts proliferated modestly, and microvascular endothelial cells proliferated profusely as shown in FIGS. 1–3, respectively. In the figures, KP stands for keratin powder with the number following representing the concentration of KP. The average indicated effect for several trials is given by the wide bars and the standard deviation is given by the narrow bars extending therefrom.

The mitogenic activity observed in fibroblast, keratinocyte, and endothelial cell cultures is evidence that the keratin powder is not only biocompatible but also mitogenic with these cell lines. Additional biocompatibility was observed when keratin microfibrils were observed microscopically to be in direct contact with cells in the cell cultures. Specifically, keratinocytes and fibroblasts were observed to adhere to and congregate around keratin microfibrils indicating that desirous cell activity can be sustained on this naturally derived bipolymer matrix.

Figure 4:
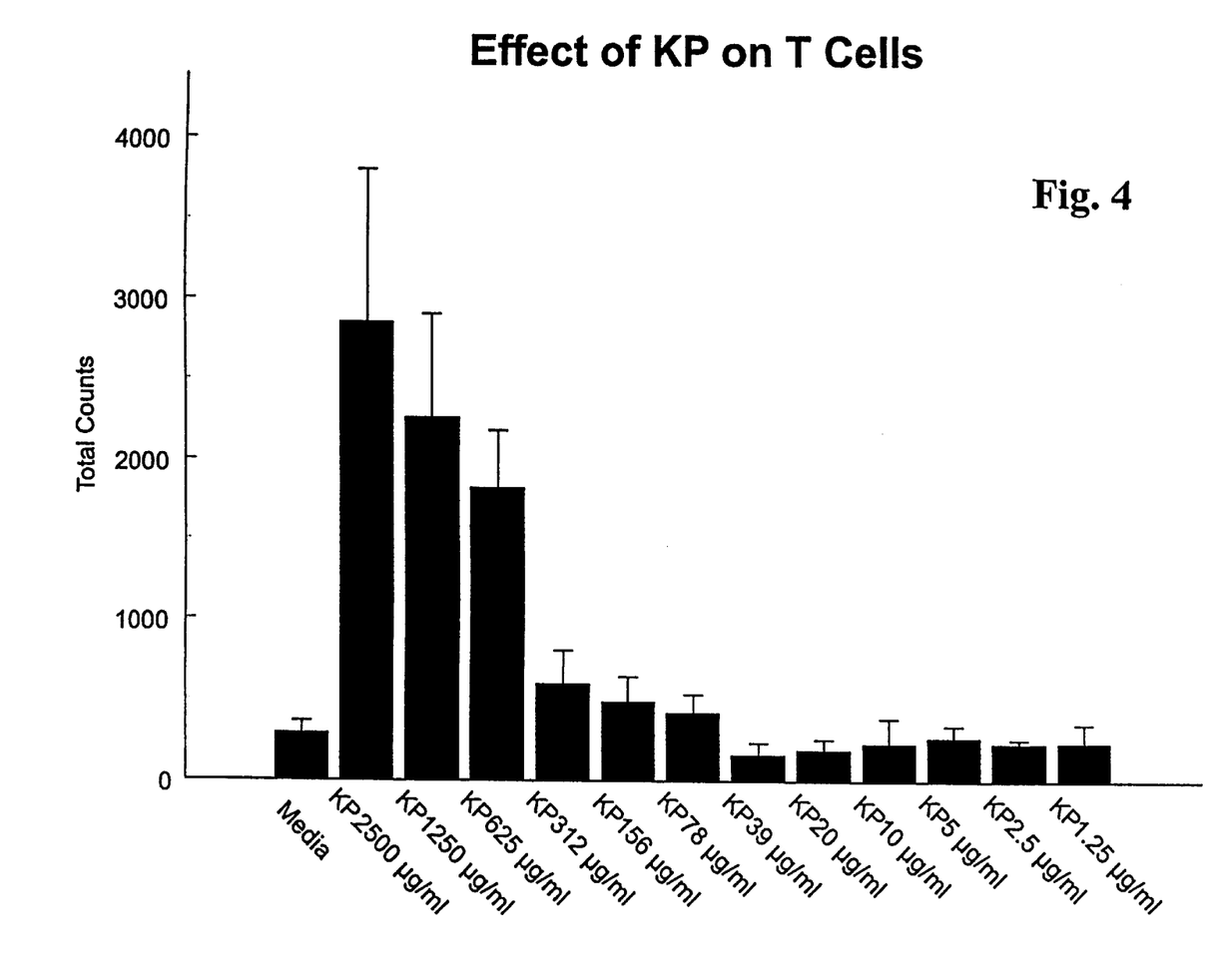
FIG. 4 is a graph showing the effect of varying concentrations of KP on T cells relative to cell media alone (media)

In a second experiment, keratin powder derived from human hair was incubated with cell culture media. The media/hair mixture was passed through a micro filter. This media extract was used in proliferation studies with lymphocytes (T cells). The lymphocyte cell line did not proliferate, indicating the material to be non-immunogenic, as shown in FIG. 4.

Figure 5:
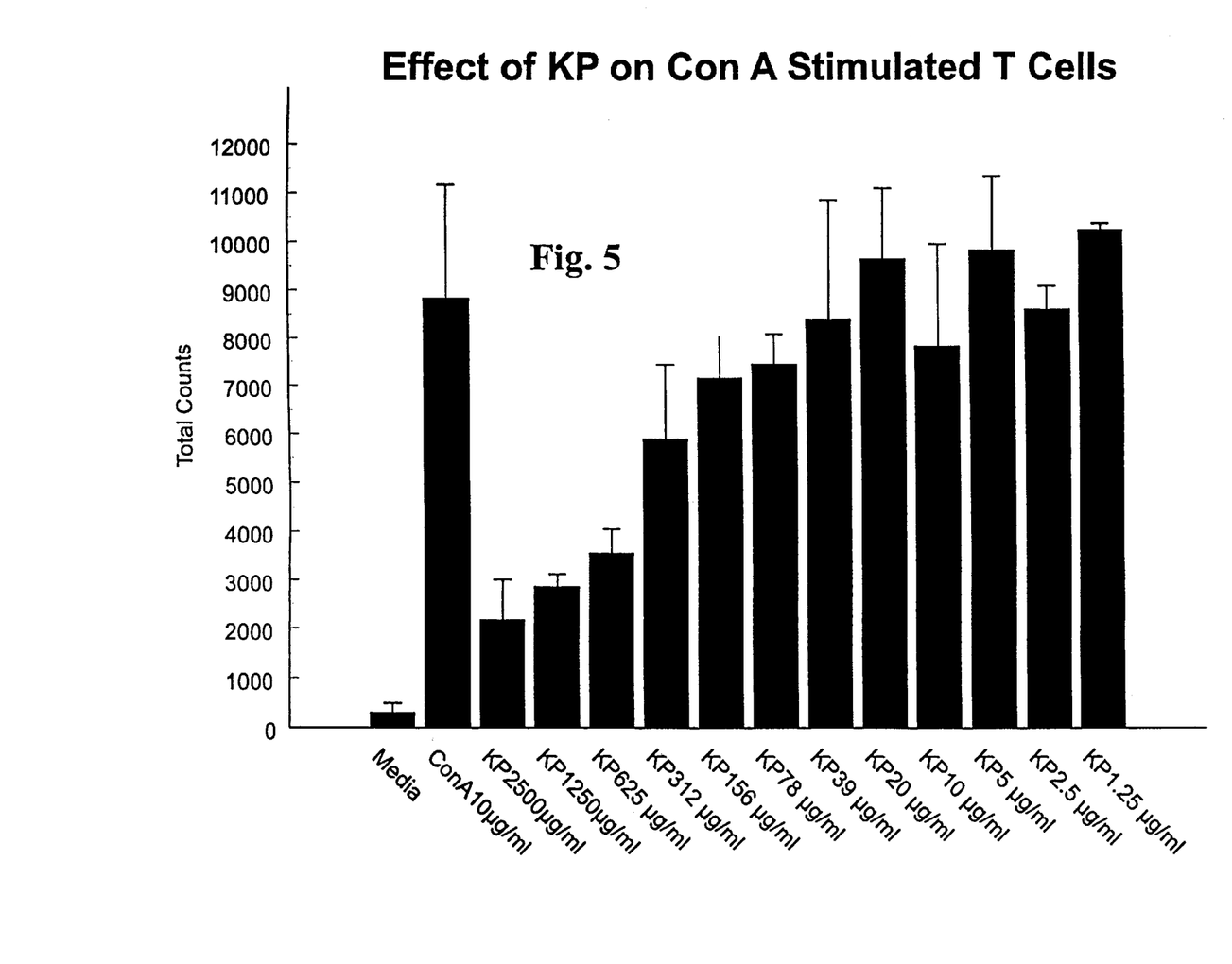
FIG. 5 is a graph showing the effect of varying concentrations of KP on Con A Stimulated T cells relative to cell media alone (media).

In a third experiment, keratin powder derived from human hair was incubated with cell culture media. The media/hair mixture was then passed through a micro filter. This media extract was used in proliferation studies with concanavlin A-stimulated lymphocytes (T cells). The stimulated lymphocytes proliferated normally, indicating no inhibition of activated T-cells by the keratin powder. This demonstrated that the body's normal cell-mediated immune response is not inhibited by the keratin. See FIG. 5.

In a fourth experiment, twenty-eight hairless rats were wounded on either side of the dorsal midline with a dermatome, creating a partial thickness wound, 0.3 cm in depth, and 2.0×4.0 cm in surface area. Half of the wounds were treated with keratin powder, half were not, and both halves were covered with polyurethane dressing. The wounds were observed for healing and biopsied at days 0, 2, 4, and 6 for histochemical analysis. Planimetry studies showed 97% epithelialization of the keratin treated wounds and 78% epithelialization of the non-treated wounds at day 4. Histological analysis by H & E stain revealed total epithelialization microscopically of the keratin treated wounds at day 2 and only partial epithelialization of the non-treated wounds at day 2. Histological analyses at days 4 and 6 also revealed an acceleration of the epithelialization maturation process in the keratin treated wounds.

In a fifth experiment, Patient A, a 57-year old white female, had a full thickness skin loss of her lower leg measuring 8×12 cm. This patient had rheumatoid arthritis and received 80 mg/day of prednisone. Since it was anticipated that this patient would exhibit a prolonged healing time due to her chronic steroid use, she was chosen for a donor site partial thickness wound study.

The wound of the left leg was prepared for skin grafting using multiple debridements and hydrotherapy. Under general anesthesia, the left leg wound was surgically debrided and covered with a split thickness skin graft from the right upper thigh. One half of the thigh wound (donor site) was treated topically with keratin powder and one half of the donor site with antibiotic ointment. The keratin-treated side of the donor site was significantly less painful and healed (epithelialized) in seven days. The non-keratin treated side epithelialized in 10 days and was subjectively more painful. In general, the keratin-treated portion of the wound demonstrated more rapid healing and less pain.

Nine additional donor sites were also studied in a variety of patients. The keratin powder accelerated healing in all patients studied.

In a sixth experiment, Patient B, a 63-year old black male with insulin dependent diabetes, developed a fall thickness skin loss (4×15 cm) of the left lower leg. This wound would not heal using local wound cleansing, topical antibiotics, elastic garments and leg elevation. This gentlemen represented a healing impaired patient (due to diabetes mellitis). His wound was chosen for a full thickness wound study.

The leg wound was treated as before, except keratin powder was applied to the wound after cleansing. Gauze, soaked in betadine solution, was applied to the wound and then wrapped with elastic bandages. He continued to elevate the leg and returned to the physicians office for dressing changes twice per week. The wound finally began to epithelialization during the course of the keratin treatment and was completely healed at the end of six weeks.

The successful treatment of this wound demonstrates accelerated healing and epithelialization of a full thickness wound in a healing impaired patient using a keratin wound healing material.

Numerous characteristics and advantages of the invention covered by this document have been set forth in the foregoing description. It will be understood, however, that this disclosure is, in many respects, only illustrative. Changes may be made in details, particularly in matters of shape, size, and ordering of steps without exceeding the scope of the invention. The invention's scope is, of course, defined in the language in which the appended claims are expressed.

What is claimed is:

1. A process for creating a wound dressing sheet comprising the steps of:
   providing a polymer binder material;
   providing a solvent;
   dissolving said polymer binder in said solvent, creating a polymer binder solution;
   providing keratin powder;
   suspending said keratin powder in said polymer binder solution, creating a keratin suspension;
   casting said suspension into a sheet; and
   flashing off said solvent.

2. A process for creating a wound dressing sheet as recited in claim 1, wherein said keratin powder includes high aspect ratio whiskers of keratin having an aspect ratio of between about 10 and about 50.

3. A process for creating a wound dressing sheet as recited in claim 1, wherein said polymer binder is selected from the group consisting of non-resorbable polymers, bioresorbable polymers and resorbable keratin.

4. A process for creating a wound dressing sheet as recited in claim 3, wherein said group of non-resorbable polymers comprises ethyl cellulose, cellulose acetate, and polyethylene.

5. A process for creating a wound dressing sheet as recited in claim 3, wherein said group of bioresorbable polymers comprises the family of polylactic acid-polyglycolic acid copolymers.

6. A process for creating a wound dressing sheet as recited in claim 3, wherein said group of bioresorbable polymers comprises resorbable keratin.

7. A process for creating a wound dressing sheet as recited in claim 1, wherein said binder is used in an amount ranging between about 3 weight percent and 50 weight percent relative to the weight of said keratin powder.

8. A process for creating a wound dressing sheet as recited in claim 1, wherein said keratin powder comprises a fine powder weight fraction and a course powder weight fraction, wherein said fine powder fraction has an average major dimension between 0.1 μm and about 100 μm and an aspect ratio ranging from about 1–4, and said course powder fraction has an average major dimension between about 100 μm and 500 μm and an aspect ratio ranging from about 10–50.

9. A process for creating a wound dressing sheet as recited in claim 8, wherein said fine keratin powder weight fraction and said course powder weight fraction are about equal, wherein said polymer binder is used in an amount of about 3 weight percent relative to the weight of said keratin powder, wherein said keratin powders are used in a concentration between about 10 volume percent and 65 volume percent relative to said solvent volume.

10. A method for treating a wound in a patient comprising applying keratin to said wound, wherein said keratin is obtained from human hair.

11. A method for treating a wound as recited in claim 10, wherein said keratin is derived from hair of said patient.

12. A method for treating a wound as in a patient comprising applying keratin to said wound, wherein said keratin is in sheet form comprising keratin bound together with a polymeric binder.

13. A method for treating a wound as recited in claim 12, wherein said sheet is formed by
   providing a polymer binder material;
   providing a solvent;
   dissolving said polymer binder in said solvent, creating a polymer binder solution;
   providing keratin powder;
   suspending said keratin powder in said polymer binder solution, creating a keratin suspension;
   casting said suspension into a sheet; and
   flashing off said solvent.

14. A method for treating a wound in a patient comprising applying keratin to said wound, wherein said keratin is created by a process comprising:
   comminuting hair into a keratin powder; and
   sterilizing said keratin powder.

15. A wound dressing comprising:
   a sheet comprising keratin powder bound with a polymeric binder.

16. A method for treating a wound in a patient comprising:
   applying keratin obtained from hair to said wound.

17. A method for treating a wound as recited in claim 16, wherein said keratin is obtained from human hair.

18. A method for treating a wound as recited in claim 16, wherein said keratin is obtained from hair of said patient.

19. A method for treating a wound as recited in claim 16, wherein said keratin is a keratin powder.

20. A method for treating a wound as recited in claim 19, wherein said keratin powder is created by a process comprising:
   comminuting hair into a keratin powder; and
   sterilizing said keratin powder.

21. A method for treating a wound as recited in claim 19, wherein said keratin powder has a major dimension ranging from about 0.1 μm to about 500 μm.

22. A method for treating a wound as recited in claim 19, wherein said keratin powder has a major dimension ranging from about 100 μm to about 500 μm.

23. A method for treating a wound as recited in claim 16, wherein said keratin is in sheet form.

24. A method for treating a wound as recited in claim 23, wherein said sheet is formed by:
   forming a suspension by combining a polymer binder material, a solvent, and a keratin powder;
   casting said suspension into a sheet; and
   flashing off said solvent.

25. A wound dressing comprising keratin powder, wherein said keratin is obtained from hair.

26. A wound dressing as recited in claim 25, wherein said hair is human hair.

27. A wound dressing as recited in claim 25, wherein said keratin powder has a major dimension ranging from about 0.1 μm to about 500 μm.

28. A wound dressing as recited in claim 25, wherein said keratin powder has a major dimension ranging from about 0.1 μm to about 100 μm.

29. A wound dressing as recited in claim 28, wherein said keratin powder has an aspect ratio from about 1–4.

30. A wound dressing as recited in claim 25, wherein said keratin powder has a major dimension ranging from about 100 μm to about 500 μm.

31. A wound dressing as recited in claim 30, wherein said keratin powder has an aspect ratio from about 10–50.

32. A wound dressing created by a process comprising:
   comminuting hair into a keratin powder; and
   sterilizing said keratin powder.

33. A wound dressing as recited in claim 32, wherein said hair is human hair.

34. A wound dressing as recited in claim 32, wherein said keratin powder has a major dimension ranging from about 0.1 μm to about 500 μm.

35. A wound dressing as recited in claim 32, wherein said keratin powder has a major dimension ranging from about 0.1 μm to about 100 μm.

36. A wound dressing as recited in claim 35, wherein said keratin powder has an aspect ratio from about 1–4.

37. A wound dressing as recited in claim 32, wherein said keratin powder has a major dimension ranging from about 100 μm to about 500 μm.

38. A wound dressing as recited in claim 37, wherein said keratin powder has an aspect ratio from about 10–50.

39. A wound dressing as recited in claim 15, wherein said keratin powder is obtained from hair.

40. A wound dressing as recited in claim 39, wherein said hair is human hair.

41. A wound dressing as recited in claim 15, wherein said keratin powder has a major dimension ranging from about 0.1 μm to about 500 μm.

42. A wound dressing as recited in claim 15, wherein said keratin powder has a major dimension ranging from about 0.1 μm to about 100 μm.

43. A wound dressing as recited in claim 42, wherein said keratin powder has an aspect ratio from about 1–4.

44. A wound dressing as recited in claim 15, wherein said keratin powder has a major dimension ranging from about 100 μm to about 500 μm.

45. A wound dressing as recited in claim 44, wherein said keratin powder has an aspect ratio from about 10–50.

46. A wound dressing as recited in claim 15, wherein said polymeric binder is a non-resorbable polymer.

47. A wound dressing as recited in claim 46, wherein said non-resorbable polymer is selected from the group comprising ethyl cellulose, cellulose acetate, and polyethylene.

48. A wound dressing as recited in claim 15, wherein said polymeric binder is a bioresorbable polymer.

49. A wound dressing as recited in claim 48, wherein said bioresorbable polymer is selected from the group comprising polylactic acid polymer, polyglycolic acid polymer, polylactic acid-polyglycolic acid copolymers and resorbable keratin.

50. A keratin wound dressing sheet created by the process comprising:

forming a suspension by combining a polymeric binder, a solvent, and a keratin powder obtained from hair;

casting said suspension into a sheet; and flashing off said solvent.

51. A keratin wound dressing sheet as recited in claim 50, wherein said keratin powder has a major dimension ranging from about 0.1 $\mu$m to about 500 $\mu$m.

52. A keratin wound dressing sheet as recited in claim 50, wherein said keratin powder has a major dimension ranging from about 0.1 $\mu$m to about 100 $\mu$m.

53. A keratin wound dressing sheet as recited in claim 52, wherein said keratin powder has an aspect ratio from about 1–4.

54. A keratin sheet wound dressing as recited in claim 50, wherein said wherein said keratin powder has a major dimension ranging from about 100 $\mu$m to about 500 $\mu$m.

55. A keratin wound dressing sheet as recited in claim 50, wherein said wherein said keratin powder has a major dimension ranging from about 100 $\mu$m to about 500 $\mu$m.

56. A keratin wound dressing sheet s recited in claim 55, wherein said keratin powder has an aspect ratio from about 10–50.

57. A keratin wound dressing sheet as recited in claim 50, wherein said polymeric binder is a non-resorbable polymer.

58. A keratin wound dressing sheet as recited in claim 57, wherein said non-resorbable polymer is selected from the group comprising ethyl cellulose, cellulose acetate, and polyethylene.

59. A keratin wound dressing sheet as recited in claim 50, wherein said polymeric binder is a bioresorbable polymer.

60. A keratin wound dressing sheet as recited in claim 59, wherein said bioresorbable polymer is selected from the group consisting of polylactic acid polymer, polyglycolic acid polymer, polylactic acid-polyglycolic acid copolymers and resorbable keratin.

61. A wound dressing as recited in claim 60, wherein said hair is human hair.

62. A wound dressing as recited in claim 60, wherein said keratin is a keratin powder.

63. A wound dressing as recited in claim 62, wherein said keratin powder has a major dimension from ranging about 0.1 $\mu$m to about 500 $\mu$m.

64. A wound dressing as recited in claim 62, wherein said keratin powder has a major dimension ranging from about 0.1 $\mu$m to about 100 $\mu$m.

65. A wound dressing as recited in claim 64, wherein said keratin powder has an aspect ratio from about 1–4.

66. A wound dressing as recited in claim 62, wherein said keratin powder has a major dimension ranging from about 100 $\mu$m to about 500 $\mu$m.

67. A wound dressing as recited in claim 66, wherein said keratin powder has an aspect ratio from about 10–50.

* * * * *

UNITED STATES PATENT AND TRADEMARK OFFICE
CERTIFICATE OF CORRECTION

PATENT NO. : 6,274,163 B1
DATED : August 14, 2001
INVENTOR(S) : Cheryl R. Blanchard et al.

It is certified that error appears in the above-identified patent and that said Letters Patent is hereby corrected as shown below:

Column 7,
Line 30, delete "as"

Column 8,
Lines 39, 42 and 47, delete the occurrence of "wherein said"

Column 9, lines 28-33 through Column 10, lines 1-16,
Delete claims 54 through 60, insert:
-- 54. A keratin wound dressing sheet as recited in claim 50, wherein said keratin powder has a major dimension ranging from about 100 μm to about 500 μm.
55. A keratin wound dressing sheet as recited in claim 54 wherein said keratin powder has an aspect ratio from about 10-50.
56. A keratin wound dressing sheet as recited in claim 50, wherein said polymeric binder is a non-resorbable polymer.
57. A keratin wound dressing sheet as recited in claim 56 wherein said non-resorbable polymer is selected from the group comprising ethyl cellulose, cellulose acetate, and polyethylene.
58. A keratin wound dressing sheet as recited in claim 50, wherein said polymeric binder is a bioresorbable polymer.
59. A keratin wound dressing sheet as recited in claim 58, wherein said bioresorbable polymer is selected from the group consisting of polylactic acid polymer, polyglycolic acid polymer, polylactic acid-polyglycolic acid copolymers and resorbable keratin.
60. A wound dressing comprising a carrier including keratin obtained from hair, said carrier selected from the group consisting of gels, lotions, and creams. --

Signed and Sealed this

Eighth Day of October, 2002

*Attest:*

*Attesting Officer*

JAMES E. ROGAN
*Director of the United States Patent and Trademark Office*